(12) United States Patent
Gedamu

(10) Patent No.: US 11,798,664 B2
(45) Date of Patent: *Oct. 24, 2023

(54) SYSTEM AND METHOD FOR MANUFACTURING CUSTOM NAILS

(71) Applicant: H3ALTH TECHNOLOGIES INC., Calgary (CA)

(72) Inventor: Elias Gedamu, Calgary (CA)

(73) Assignee: H3ALTH TECHNOLOGIES INC., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,751

(22) Filed: Nov. 21, 2022

(65) Prior Publication Data
US 2023/0079330 A1 Mar. 16, 2023

Related U.S. Application Data

(63) Continuation of application No. 16/624,899, filed as application No. PCT/CA2018/050753 on Jun. 21, 2018, now Pat. No. 11,515,019.

(Continued)

(51) Int. Cl.
*G16H 10/65* (2018.01)
*G16H 50/30* (2018.01)
(Continued)

(52) U.S. Cl.
CPC ............. *G16H 10/65* (2018.01); *A45D 31/00* (2013.01); *G06T 17/00* (2013.01); *G16H 50/30* (2018.01);
(Continued)

(58) Field of Classification Search
CPC ....... G06K 19/06065; G06K 19/06037; G06K 19/06075; G06K 7/1417; G06K 7/1486; G06Q 30/06
(Continued)

(56) References Cited

U.S. PATENT DOCUMENTS

| 9,799,116 B2* | 10/2017 | Kafuku | G06T 7/73 |
| 2013/0174862 A1* | 7/2013 | Samain | B29C 64/386 |
| | | | 132/73 |
| 2019/0191845 A1* | 6/2019 | Sasaki | G06T 7/12 |

FOREIGN PATENT DOCUMENTS

| JP | 2016137039 A | * | 8/2016 |
| JP | 2017099467 A | * | 6/2017 |

* cited by examiner

*Primary Examiner* — Edwyn Labaze
(74) *Attorney, Agent, or Firm* — Bryce W. Burnham; BOOTH UDALL FULLER, PLC

(57) ABSTRACT

A system and method for manufacturing custom fit artificial nails includes a 3D surface scanning module and a 3D printing module and use thereof. A central processing module is connected to the 3D surface scanning module and the 3D printing module and performs: operating the 3D surface scanning module to obtain an image of a user's hands/feet; processing the image to create an input 3D model of nails of the user; generating an output 3D model corresponding to artificial nails matching dimensions of the user's nails according to the 3D input model; operating the 3D printing module to manufacture artificial nails according to the output 3D model; and generating medical data by correlating the identified features of the user's nails with known medical conditions, in order to diagnose a medical condition of the user which is known to exhibit the identified features as a symptom. Alternatively, or additionally, medicinal ingredient may be included in the artificial nail to treat the medical condition of the user. Embedded devices, sensors or an RFID chip may be integrated into the artificial nail.

20 Claims, 5 Drawing Sheets

Related U.S. Application Data

(60) Provisional application No. 62/522,906, filed on Jun. 21, 2017.

(51) Int. Cl.
  *H04W 4/80* (2018.01)
  *A45D 31/00* (2006.01)
  *G06T 17/00* (2006.01)
  *B33Y 10/00* (2015.01)
  *B33Y 80/00* (2015.01)

(52) U.S. Cl.
  CPC ............... *H04W 4/80* (2018.02); *B33Y 10/00* (2014.12); *B33Y 80/00* (2014.12)

(58) Field of Classification Search
  USPC ................................................ 705/3, 2, 27.1
  See application file for complete search history.

Extends Beyond
Nail Border

SYSTEM AND METHOD FOR MANUFACTURING CUSTOM NAILS

RELATED PATENT APPLICATION

The present application is a Continuation of U.S. patent application Ser. No. 16/624,899, filed Dec. 19, 2019 (issued as U.S. Pat. No. 11,515,019), which is the U.S. National Stage of International Patent Application No. PCT/CA2018/050753, filed Jun. 21, 2018, which claims priority from U.S. Provisional Patent Application No. 62/522,906, filed Jun. 21, 2017, the contents of each of which are hereby incorporated by reference in their entireties.

TECHNICAL FIELD

The technical field generally relates to 3D imaging and nail manufacturing.

BACKGROUND 3D imaging has become the de facto standard for digitizing real world objects (e.g. shoes, compressors, brains, mapping, and planetary topology) across varying fields of interest (e.g. clothing and fashion, medical, oil and gas, geomatics, and gaming). The conversion of visual data into digital data has enabled innovative solutions in several fields of technology including Google's street view, 3D printing of a human heart, rapid prototyping, brain image analytics for neurological diseases, and the realism of video games like EA Sports' FIFA Football. While 3D imaging has had a strong impact on several industries, it is still limited as a solution for the common individual where the trend is towards customized products for their body and increased individuality.

SUMMARY

The present invention relates to a concept for an innovative 3D scan, image, and print (3DSIP) system for producing customized nails. Each component described can be used as a standalone system (i.e. the nail scanner, image processing system, and 3D printer can be used as individual solutions) or in combination with each other (e.g. a nail scanner combined with image processing, image processing with a 3D printer, nail scanner with a 3D printer, nail scanner with image processing with a 3D printer).

Broadly described, the technology allows a user to simply choose a nail style and design using a digital user interface, scan their hands or feet in a nail scanner, and retrieve custom printed nails from a 3D printer. The technology greatly simplifies the process of creating customized nails.

The present system applies 3D imaging and printing to benefit the common individual by providing a fast, convenient, user friendly and economic way to manufacture custom-fitted artificial nails. The 3DSIP system provides further advantages by integrating powerful medical diagnostic tools in a consumer product, and by providing means to securely and conveniently manage personal electronic information through the integration of an RFID chip and/or embedded devices and sensors into artificial nails.

According to one aspect, there is provided a system for manufacturing custom fit artificial nails. The system includes a 3D surface scanning module, a 3D printing module, and a central processing module operatively connected to the 3D surface scanning module and the 3D printing module. The central processing module is operable to operate the 3D surface scanning module to obtain an image of a user's hands or feet, process the image to create an input 3D model of nails of the user, generate an output 3D model corresponding to artificial nails matching dimensions of the user's nails according to the 3D input model, operate the 3D printing module to manufacture artificial nails according to the output 3D model, process the image to identify one or more predetermined features of the user's nails, and generate medical data by correlating the identified predetermined features of the user's nails with known medical conditions, in order to diagnose a medical condition of the user which is known to exhibit the identified features as a symptom.

According to another aspect, there is provided a system for manufacturing custom fit artificial nails. The system includes a 3D surface scanning module, a 3D printing module, and a central processing module operatively connected to the 3D surface scanning module and the 3D printing module, the central processing module being operable to operate the 3D surface scanning module to obtain an image of a user's hands or feet, process the image to create an input 3D model of nails of the user, generate an output 3D model corresponding to artificial nails matching dimensions of the user's nails according to the 3D input model, receive a medical condition of the user, and operate the 3D printing module to manufacture artificial nails according to the output 3D model, the artificial nails having at least one medicinal ingredient for treating the medical condition of the user.

According to yet another aspect, there is provided a method for manufacturing custom fit artificial nails. The method includes obtaining a 3D surface scan image of a user's hands or feet, processing the image to create an input 3D model of the user's nails, generating an output 3D model corresponding to artificial nails matching dimensions of the user's nails according to the 3D input model, 3D printing artificial nails according to the output 3D model, processing the image to identify predetermined features of the user's nails, and generating medical data by correlating identified predetermined features of the user's nails with known medical conditions, in order to diagnose a medical condition of the user which is known to exhibit the identified features as a symptom.

According to yet another aspect, there is provided a method for manufacturing custom fit artificial nails in which the method includes obtaining a 3D surface scan image of a user's hands or feet, processing the image to create an input 3D model of the user's nails, generating an output 3D model corresponding to artificial nails matching dimensions of the user's nails according to the 3D input model, receiving a medical condition of the user, and 3D printing the artificial nails according to the output 3D model, the artificial nails having at least one medicinal ingredient for treating the medical condition of the user.

According to various exemplary systems described herein, the 3D printing module comprises an embedder configured to embed a premanufactured object into the artificial nails during the 3D printing process.

Various exemplary methods described herein further includes embedding a premanufactured object into the artificial nails during the 3D printing of the artificial nails.

According to various exemplary systems described herein, the premanufactured object comprises at least one of an embedded device and a sensor, and the central processing system is further operable to link to the embedded device or the sensor with a user account stored on a remote server.

According to various exemplary methods described herein, the premanufactured object comprises at least one of an embedded device and a sensor, and wherein the method further comprises linking the embedded device or the sensor with a user account stored on a remote server.

According to various exemplary systems and methods described herein, the embedded device or the sensor comprises an RFID chip.

According to various exemplary systems and methods described herein, the sensor is configured to detect the artificial nail becoming detached and to disable the RFID chip upon detecting the nail becoming detached.

According to various exemplary systems and methods described herein, the account on the remote server comprises medical information of the user.

Various exemplary systems described herein further include a network module operatively connected to the central processing module, the central processing module being configured to communicate with an online medical system over the network module in order to link the generated medical data therewith.

According to various exemplary systems described herein, the central processing module is configured to transmit the medical data to an external server over the network module in order to allow the user to access the medical data remotely and assess their medical health information.

Various exemplary methods described herein further include transmitting the medical data to an external server over a network module in order to allow the user to access the medical data remotely and access their medical health information.

According to various exemplary systems described herein, the central processing module is further configured to generate at least one of a medical forecast, a medical risk assessment and a recommendation based on the generated medical data.

Various exemplary methods described herein further include generating at least one of a medical forecast, a medical risk assessment and a recommendation based on the generated medical data.

According to various exemplary systems described herein, the central processing module is configured to store a history of scans by the user, and combine said history of scans in order to generate a model of the user's hands or feet.

Various exemplary methods described herein further include storing a history of scans by the user, and combining said history of scans in order to generate a model of the user's hands or feet.

According to various exemplary systems described herein, the central processing module is configured to analyse the history of scans in order to track a progression of the medical condition of the user.

Various exemplary methods described herein further include analyzing the history of scans in order to track a progression of the medical condition of the user.

According to various exemplary systems described herein, the central processing module is configured to store a history of scans by a plurality of users, and combine said history of scans in order to build a population model representing variability across the plurality of users.

According to various exemplary systems described herein, the central processing module is configured to compare the image of the user's hands or feet with the population model in order to determine differences there between.

Various exemplary methods described herein further include comparing the image of the user's hands or feet with the population model in order to determine differences therebetween.

According to various exemplary systems and methods described herein, processing the image to identify predetermined features of the user's nails comprises identifying nail features selected from the group consisting of: anatomical changes, color, thickness, splitting, concavity, pitting, ridges, dryness and clubbing.

According to exemplary various systems described herein, the 3D surface scanning module comprises at least one sensor of a first type operable to capture shapes of the nails of the users and at least one sensor of a second type operable to capture surface features of the nails of the user.

Various exemplary systems described herein further include a user interface module operatively connected to the central processing module, the user interface module allowing the user to customize a design of the artificial nails to be printed.

Various exemplary methods described herein further include presenting a user interface module allowing the user to customize a design of the artificial nails to be printed.

According to various exemplary systems described herein, the security, privacy, and interoperability of the data and system is ensured using blockchain.

According to various exemplary systems described herein, the 3D printing module is operable to add at least one medicinal ingredient to the manufactured artificial nail.

Various exemplary methods described herein further include comprising adding at least one medicinal ingredient to the manufactured artificial nail.

According to various exemplary systems described herein, the central processing module is operable to select the medicinal ingredient based on the medical condition diagnosed for the user.

Various exemplary methods described herein further include selecting the medicinal ingredient based on the medical condition diagnosed for the user.

According to various systems and methods described herein, the medicinal ingredient comprises an antifungal component.

BRIEF DESCRIPTION OF THE DRAWINGS

Embodiments will be described in greater detail with reference to the accompanying drawings, in which like reference numerals indicate like elements, and wherein.

DETAILED DESCRIPTION

Figure 1:
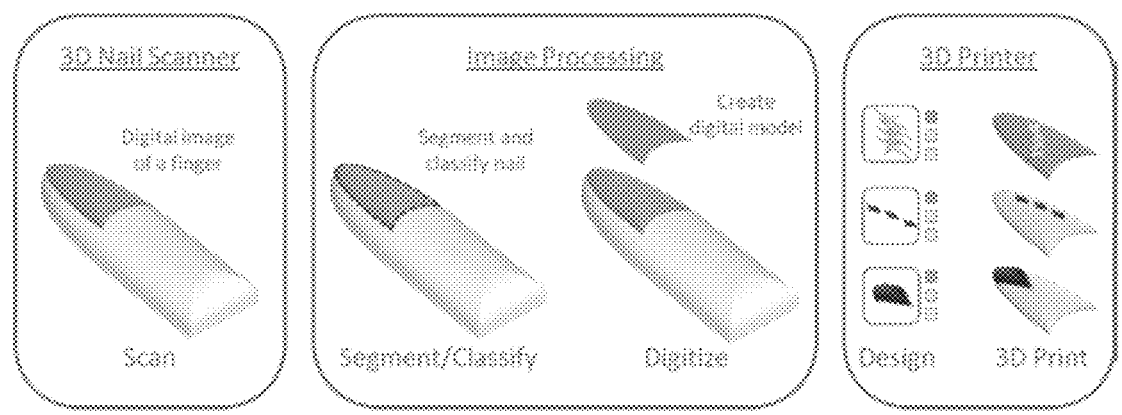
FIG. 1 is a schematic illustrating a process for scanning, processing, and printing custom-fit artificial nails.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

With reference to FIG. 1, the main steps of a nail scanning and printing procedure are illustrated according to an embodiment. In a first step, a user's nails are scanned in order to create a digital image of the user's fingers. The nails can be scanned, for example, by scanning individual fingers/toes one at a time, or by scanning one or two hands/feet at a time in order to capture many fingers/toes simultaneously. Next, a processing step involves segmenting and classifying the digital images in order to create exact digital 3D models of the user's nails, the 3D models preferably having the exact anatomical dimensions of the scanned nails. Several image processing algorithms and quality control (QC) procedures can be used to ensure the accuracy of the model process. Preferably, the accuracy of the modelling process is within the acceptable parameters of the artificial nail which will be produced. Finally, once the 3D models have been created, artificial nails are printed using a 3D printer, according to the 3D models. Prior to printing, users can customize the design of the artificial nails, for example by selecting various shaped, patterns, colors, etc.

Figure 2:
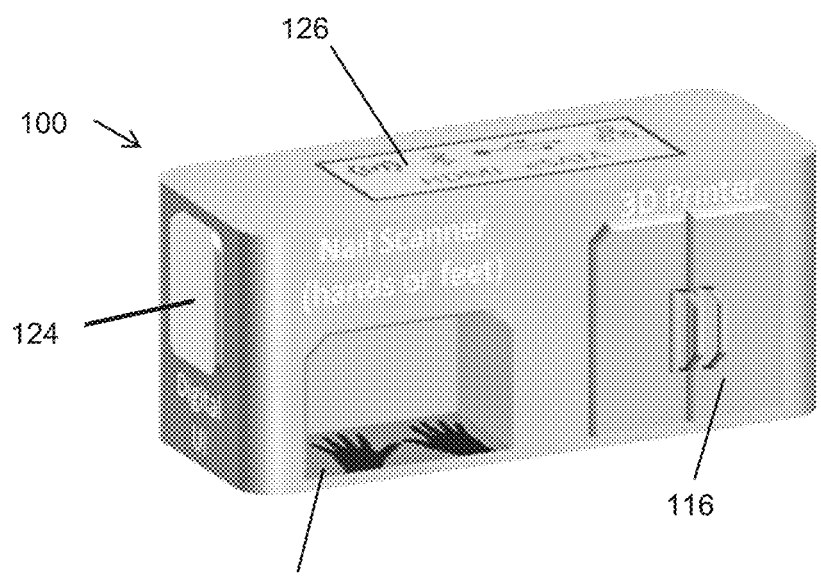
FIG. 2 is a schematic illustrating a system for scanning, processing and printing custom-fit artificial nails, according to an embodiment.
Figure 3:
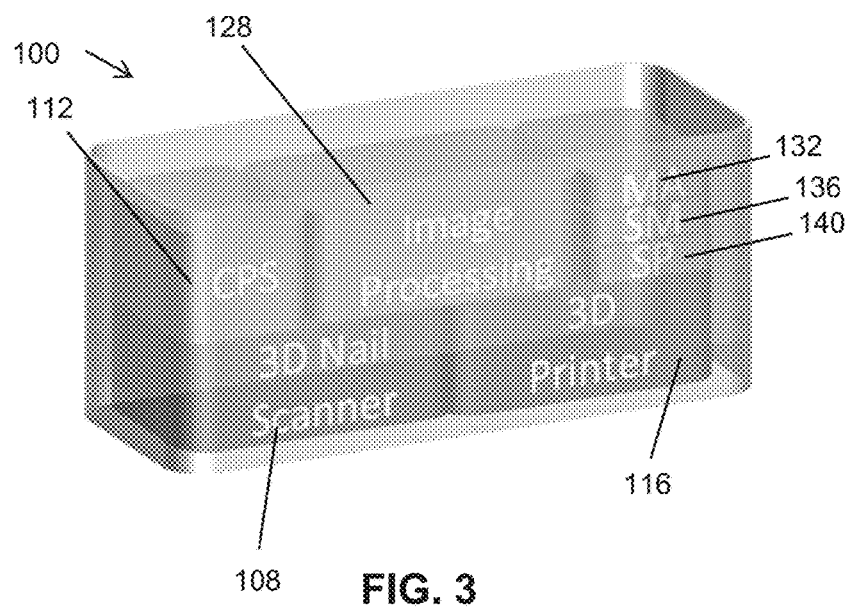
FIG. 3 is a block diagram illustrating hardware and processing modules implemented in the system of FIG. 2.

With reference to FIGS. 2 and 3, a 3DSIP system 100 is provided for implementing the above-described process. The system comprises a 3D scanning module 108, a central processing system (CPS) 112, a 3D printing module 116, a user interface (UI) module 124, and connection ports 126. Generally speaking, the 3D scanning module serves to scan a user's nails with a high level of accuracy in order to build a 3D model thereof, and the 3D printer builds custom nails form-fitted to the user according to the 3D model. The 3D printed nails can be customized by the user through the UI module, which can allow users to interact with the system and design the appearance of the artificial nails prior to printing. The CPS integrates all of the hardware components together, and can perform required functions such as image processing procedures 128, medical analytics (MA) 132, social media (SM) integration 136, and solution package (SP) integration 140, which will be described in more detail hereafter. The connection ports 126 allow the system to interact with other devices and networks, such as a local area network (LAN), wide area network (WAN) or the internet, for example over wired or wireless interfaces, such as Bluetooth, Bluetooth LE, swarm intelligence, universal serial bus (USB), high-definition multimedia interface (HDMI), external serial advanced technology attachment (eSATA), wifi, mobile, satellite. It is appreciated that other types of connections are also possible. The connection ports 126 can allow connection to a mobile device, such as a smartphone, tablet, smart watch or video game device, to present a user interface thereon. The user interface can be used to design the artificial nails and/or view medical data, as described elsewhere herein.

3D nails can be designed using other digital systems like personal computers or smart devices and then uploaded on the 3DSIP system 100 for printing. It is appreciated that the nails can be imaged using the 3DSIP system 100 and stored for printing later. Printing can be done at print shops for pick-up or delivery. This facilitates repeat orders on preferred nail designs.

Figure 4:
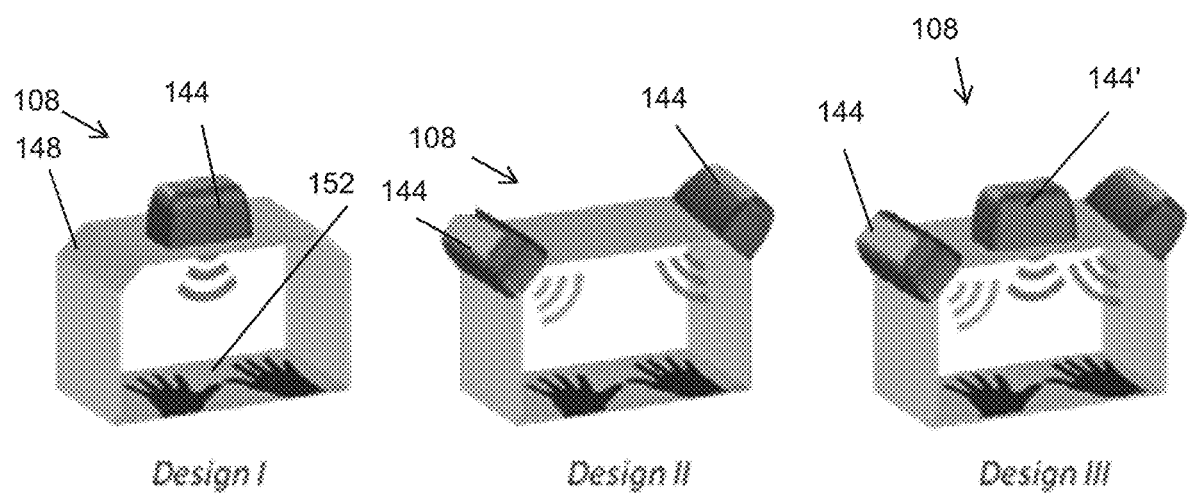
FIG. 4 are schematics illustrating a scanning module according to three different embodiments, each having a different sensor configuration.

The 3D scanning module 108 can include a 3D surface scanner 144 to acquire nail data by producing an image of the outer layer of a user's fingers or toes. In some embodiments, for example as illustrated in FIG. 4, the 3D scanning module can include a frame 148 for supporting one or a plurality of surface scanning sensors 144. The 3D scanning module 108 can further include a platform 152 for supporting a user's hands or feet during the scan.

It should be understood that the frame 148 can have various shapes and can be made of various materials. Preferably, the frame 148 is configured so as to allow the sensors to fully capture images of a user's hands/feet. Preferably still, the frame is configured so as to not interfere with the sensors. For example, in the case of a laser-based sensor for scanning, the frame should not be made of a highly light-reflective material, which would be a likely source of error. Finally, the frame should be made sturdy so as to support the sensors, and so as to avoid movement, for example to prevent errors due to vibration during a scan.

Moreover, several types, shapes and materials of platforms can be used. Preferably, the platform should be configured to maximize a line of sight between the sensors 144 and the object being scanned, while ensuring comfort and limiting the movement of the hands during the scan. For example, the platform 152 can be made of a sturdy material, allowing hands or feet to be rested stably thereon. The platform 152 can include marking and/or small indentations to guide users in properly placing and orienting their hand/feet, and encouraging users to spread their fingers/toes to facilitate image processing thereafter. Preferably, the platform design 152 should not limit the image processing process, for example by introducing systematic error. As with the frame, the platform 152 should not be made of a material which is likely to interfere with the sensors used for scanning. Preferably, the platform 152 should have an even surface and/or be planar such that all parts of an object can be scanned in a similar frame of reference.

As shown in FIG. 4, several different designs of the scanning module 108 are possible. In each of the designs, the platform 152 is connected to the frame 148 and forms a base thereof. However, in some embodiments, the platform 152 can be separate from the frame 148. Moreover, in the illustrated designs, the frame 148 has a particular shape to hold sensors at various positions and angles. It is appreciated that this shape can vary according to the type, number and desired arrangement of sensors 144.

One or several different sensors can be used in tandem or separately in order to capture surface images. Moreover, a plurality of different sensor types can be used in order to capture several images using different scanning methods/technologies. For example, Design I shows a scanning module 108 which uses one sensor 144, secured to the frame 148 opposite the scanning platform 152. Design II shows a scanning module 108 with two identical sensors 144 secured to opposite ends of the frame 148, and angled towards the scanning platform 152. Design III shows a scanning module with two sensors 144 of a first type secured to opposite ends of the frame and angled towards the scanning platform, and a third sensor 144' of a second type secured to the frame opposite the scanning platform. It is appreciated that these are exemplary configurations only, and that sensor number and positioning can vary.

Furthermore, the sensors 144 can be positioned and configured to work together to capture a single image, for example by having overlapping fields of view, by scanning simultaneously and/or by providing a stereoscopic view of the same object. In some configurations, each sensor or each group of sensors can capture images individually, for example by having mutually exclusive fields of view, or by capturing images at different times. It is appreciated that images captured by the sensors, whether captured individually or in tandem, can be combined in order to obtain a more accurate 3D scan. Moreover, different types of sensors can be used to capture different information. For example, a first sensor type can be used to capture surface shape/dimensions, whereas other sensor types can capture more precise surface features, such as colors and visual patterns/textures and heat, or perform a more detailed scan on smaller, more specific areas of the object being scanned. Some sensors can further be used to detect features underneath the outer surface of the object being scanned. In another embodiment, a motor can be used to enable sensors to traverse over the object of interest (i.e. hands and/or feet) to capture 3D data. This would be a non-stationary system.

In other embodiments, a single or plurality of sensors could be attached to a mobile phone, integrated within a mobile phone, or a combination thereof to enable a portable mobile version of the imaging device. Sensors could vary in type (e.g. depth, time of flight, photogrammetry, structured light, infrared, full spectrum, thermal sensors).

A variety of different sensor types can be used. More particularly, any frequency-based hardware component, such as infrared (IR), laser, sound, light, thermal, and photo, can be suitable for scanning. A combination of different sensor types can be used to enhance image data, for example by combining a digital camera and an IR sensor. The data can be acquired simultaneously (e.g. images are acquired using sensor type I and II simultaneously) or scanned separately and then combined later (e.g. the image can be acquired initially with sensor Type I and then with sensor Type II, or the image can be acquired over multiple time points and then combined). Sensor types with varying accuracy profiles (e.g. error rates of 300 µm to 5000 µm) can be used to provide various models and product lines (for example, some industries may not need scanners with high accuracy while others like medical diagnostics would).

Once a digital image has been acquired using the 3D scanning module 108, it can be turned into a 3D model using the CPS 112 which can implement an image processing module 128. It is appreciated that the image processing module executes a suite of processing steps, including: segmentation and classification, digitization, smoothing, texturing, image optimization, design integration, space optimization and medical diagnostics. It is appreciated that the processing steps can be performed on the cloud or the 3DSIP system 100.

The step of segmentation and classification involves delineating the nails from all other objects in the image, and classifying the nail by name (i.e. for the hand: thumb, index, middle, ring, and baby, for the feet: first, second, third, fourth, and fifth toe) and location (i.e. left or right side of the body).

The step of digitization involves using the segmented images to create a digital model of the user's nails with the exact topology and anatomical boundaries thereof. A subsequent digital model can be created for artificial nails whose shape/dimensions conform to the topology and anatomical boundaries of the scanned nails.

The step of modelling involves creating a model using every hand/foot image acquired over time for each user. For example, a user can be identified when performing a scan and a history of scans can be retained in order to build this model. A model for each finger (i.e. thumb, index, middle, ring, and baby), toe (i.e. first, second, third, fourth, and fifth toe), and respective nails can also be created. The accuracy of the model can increase as the number of scans increase. Individual scans can also be combined to build population models (i.e. images that detail the variability across the populations and provide a method for comparing data from individual images). It is appreciated that one application of this data can be for monitoring the state of nails over time and identifying medical conditions, as will be described in more detail hereinafter.

Figure 5:
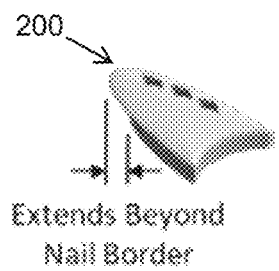
FIG. 5 illustrates the dimensions of a 3D printed custom-fit artificial nail in relation to a user's actual nail.

The texturing step involves optionally applying a texture to the bottom surface of the digital model of the artificial nails. The texture can span along the bottom surface of the artificial nails, from the border of the original nails to the end of the originals nails. With reference to FIG. 5, the artificial nail 200 could extend beyond the anatomical boundary of the user's actual nail. In this case, the texture could be applied up to the border of the user's nail (i.e. the texture would cover the same area and dimensions defined by the person's nail) or where the finger terminates. It is appreciated that this can increase adhesions between the printed artificial nail and the user's actual nail.

The image optimization step involves compressing the images to a level that retains all pertinent data while facilitating data transfer between the 3DSIP, cloud, and smart device. It is appreciated that image optimization may not be used in cases where uncompressed data could be beneficial for processing like medical analytics.

The design integration step involves applying custom designs to the digital artificial nails. This can involve altering the shape and/or surface decoration of the digital artificial nails, and/or adding additional features to the artificial nails, for example according to the design specified by the user. The design integration can be applied to each artificial nail individually, thereby allowing the design to conform to each type of nail, and allowing for different designs to be applied to different nails, according to the user's specifications. In some embodiments, the design applied to the artificial nail can mimic the look of the user's natural nail. For example, nails that are impacted by fungal infections can have a different color and/or texture compared to healthy nails. Upon detection of a fungal-infected nail with a yellowish color, an artificial nail can be printed with an appearance corresponding to a healthy color and texture. For example, this healthy color and texture can be determined based on the color of other healthy nails of the same user, or based on a previous scan of the same nail at a point in time when the nail was healthy. Thus, the printed nail structure can be used to cover up an infected nail while providing a similar natural appearance compared to the other healthy nails and porous structure to promote healing.

Figure 6:
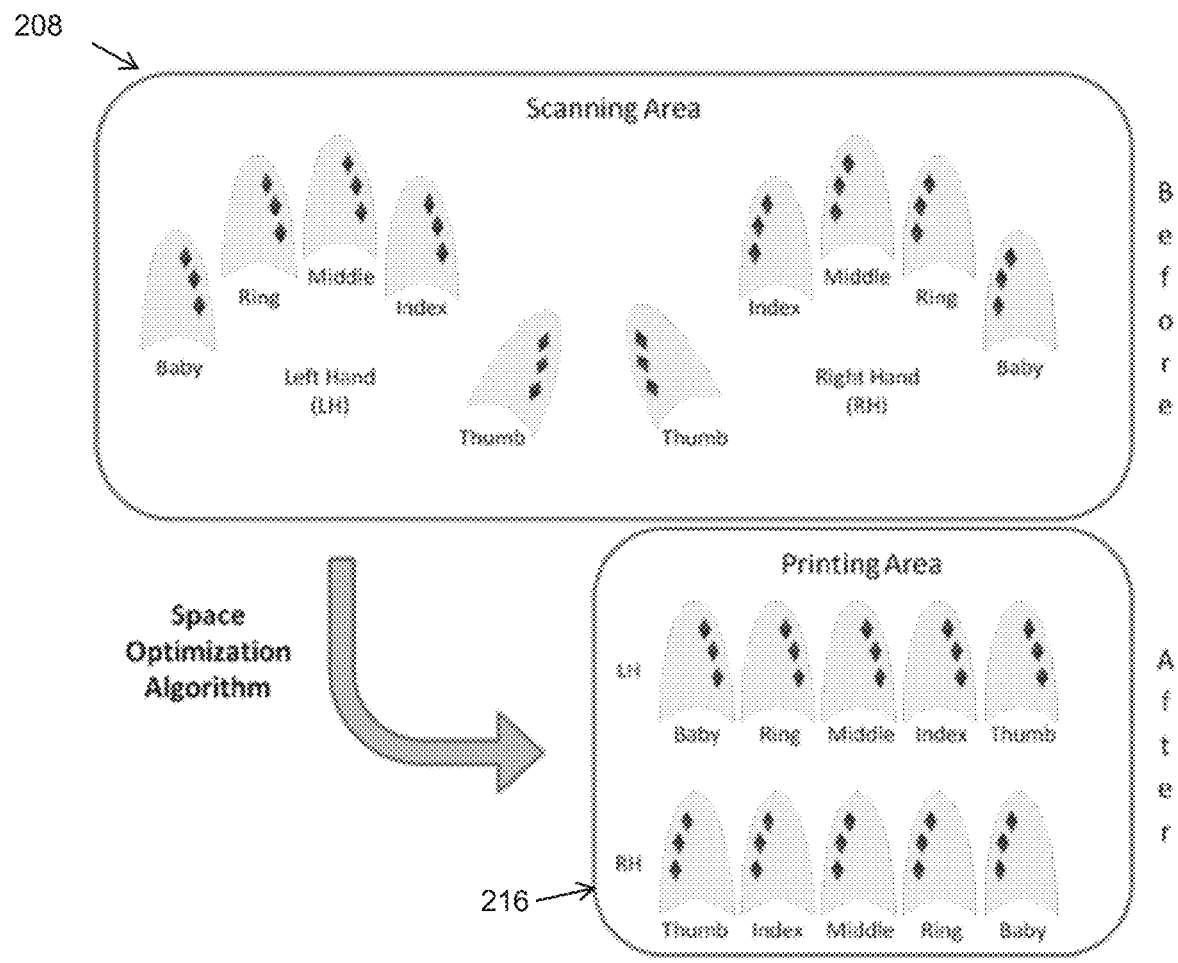
FIG. 6 is a schematic illustrating the results of a space optimization step for optimizing the printing area of artificial nails.

The space optimization step involves ensuring that the layout of the digital artificial nails is optimized for 3D printing. With reference to FIG. 6, it is appreciated that the scanning area 208 can be larger than the printing area, and that in most cases the printing area will be a limiting factor. The space optimization algorithm resolves this issue and allows all the nails to be printed in one session. Prior to the algorithm, the nails are spread out across the scanning area (before image) 208. After the algorithm is applied, the nails are optimally spaced and contained within the boundaries of the print area (after image) 216. The algorithm maximizes the utilization of space based on the design requirements. It is appreciated that variations in nail designs could result in different layouts for the printing.

The quality control step involves assessing the anomalies in the 3D nail image after the acquisition process and removing them to leave a high fidelity image; an image of the nail that is not affected by systemic errors. In some embodiments, the image of the nails is affected by movement artifacts or non-uniform image contrast which can lead to inaccurate or misrepresented printed nails. Upon detection of these types of anomalies, the quality control process corrects the errors and ensures a high fidelity image.

Once a 3D model of the artificial nails has been created, the artificial nails can be manufactured using the 3D printing module 116. It is appreciated that the 3D printing module can comprise a 3D printer which makes use of one or several additive manufacturing types, such as extrusion, light polymerized, powder bed, laminated, powder fed, and wire fed. Some 3D technologies which can be used include Stereolithography (SLA), Digital Light Processing (DLP), Fused Deposition Modeling (FDM), Selective Laser Sintering (SLS), Selective laser melting (SLM), Electronic Beam Melting (EBM) and Laminated object manufacturing (LOM).

In an embodiment, the 3D printing module 116 can employ an extrusion-type printer. It is appreciated that such a printer could use typical components that are currently used in the industry. The extrusion printer can include a frame to support the various components, an extruder to allow a printing material to be pushed or pulled to form a steady stream of workable material for print, mechanical parts to allow the printer head to move in multiple directions while printing, motors for the spatial movement and extruder, electronics (e.g. a computer or controller) to control the printing process, power to drive the load requirements, firmware for the electronics to communicate with and provide directives to each component (e.g. motors, extruder, and print header), and software for the user to interface with the printer (e.g. to select the 3D design to be printed).

The 3D printing module 116 can vary from existing extrusion-type 3D printers in that one or several extruder types may be provided, preferably allowing various different material types (such as plastic, acrylic, gel, shellac, steel, copper, etc.) to be deposited in various states (such as powder, liquid, molten, etc.) Multiple nail-specific extruders can be provided for various nail materials, and multiple extruders and/or printing heads can be provided to print several nails simultaneously. It is further appreciated that an extrusion-type 3D printing mechanism can be combined with other 3D printing mechanisms in order to print different elements.

In some embodiments, the printing material can include medicinal ingredients in addition to a matrix, to potentially treat an unhealthy nail. For example, when the system identifies that one of the user's nail has a fungal infection, the artificial nail printed for that one of the user's nails can include an antifungal component. The antifungal component can, for example, be added to a polymer matrix forming the artificial nail during the 3D printing process. In this fashion, when the user applies the artificial nail, it can serve to treat the fungal infection. Similar medical additives could be used for other conditions as well.

Furthermore, the 3D printing module 116 can also be provided with color printing capabilities. In some embodiments, the color printing can be achieved by varying a color of the 3D printing material as it is being deposited to form the artificial nails. Some embodiments can include surface area printing capabilities, whereby once a 3D artificial nail has been manufactured, full color designs can be printed directly to the surface of the nail.

The 3D printing module 116 can further be provided with an embedder, which allows items to be embedded within the artificial nails during the printing process. Items which can be embedded include gems, stones, and colors. Such items can be embedded such that they are visible on the top surface of the artificial nail, adding additional design features/decoration to the artificial nails as chosen by users. Preferably, the items should be embedded such that they are spaced-apart from the bottom surface of the artificial nails, so that embedding these items do not have an effect on the adherence of the artificial nail to the user's nails.

In some cases, the embedder can embed functional components into the artificial nail (e.g. RFID, wearable technology, sensors (e.g. heart rate monitor), etc.). For example, the embedder can be configured to embed a radio frequency identification (RFID) chip, thereby turning the artificial nail into a smart nail. Preferably, the RFID chip is embedded within the thickness of the artificial nail, thereby hiding the RFID chip from view. However, it is appreciated that the RFID chip can be positioned on the bottom surface of the nail, and thus be hidden underneath the artificial nail when it is adhered to the user's nail. In some cases, the RFID chip can be visible on the top surface of the artificial nail, and can be integrated into a decorative element, such as a gem, a stone, or a color/texture pattern.

Figure 7:
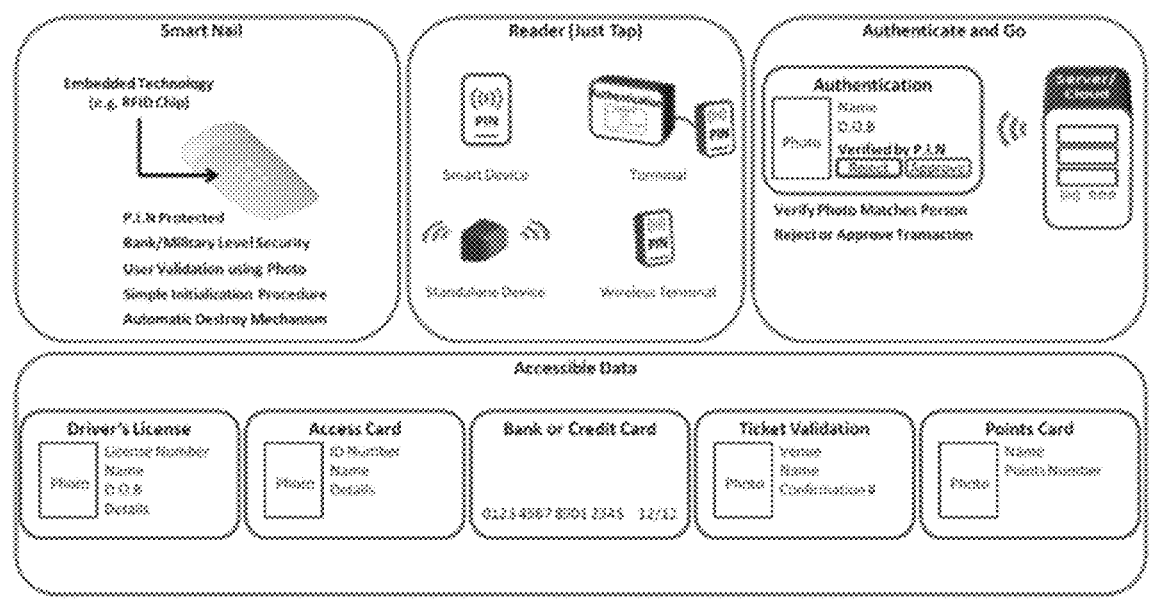
FIG. 7 is a schematic illustrating the functionality of a smart nail, made possible by integrating an RFID chip or other embedded devices or sensors into an artificial nail during the 3D printing process.

Preferably, when embedding the RFID chip, the 3DSIP system 100 should link the tag to a secure database. For example, the user can set up an account which is stored in a cloud database, and this account can be linked to the embedded RFID chip. As illustrated in FIG. 7, this can enable facilitated transaction through a "just tap, authenticate, and go" process. A user can just tap their smart nail on a reader (i.e. similar to tapping a credit card on a reader at a convenience store) and enters their personal identification number (P.I.N). The data is transferred to a server/cloud system which can use bank/military level security protocols for authentication, the data is processed and the authentication results are returned. The authentication results can include a photo of the person (retrieved from the department of motor vehicle driver's registry), and the recipient (e.g. teller, sales person, officer) can verify that the photo matches the person (e.g. client, customer) and either accepts (i.e. photo matches person) or rejects (i.e. photo does not match person) the verification.

A user can provide various types of personal information to be stored in the user account and associated with the RFID chip. It is appreciated that 3rd party accounts and services can also be associated with the user's account. For example the smart nail can be linked to a driver's license (i.e. the system can tie into the registry at the department of motor vehicles), points/loyalty card (e.g. Aeroplan, Air Miles, Chapter's), bank or credit card, access card (e.g. for the gym or work), ticket validation (i.e. a purchased event ticket can be registered to the smart nail account and verified by scanning the nail upon arrival at the game), and the like. One smart nail can be linked to multiple types of information, allowing several types of personal information to be stored in a single accessible location, and allowing one chip to account for multiple cards/services. Alternatively, different RFID chips can be embedded into multiple artificial nails within the set of nails, and associated with different information, allowing the user to have multiple smart nails, each performing different tasks and having different information associated therewith.

Further safety features can be provided to protect a user's personal information in case of a smart nail breaking or falling off. For example, a manual or auto-destroy mechanism can be provided to terminate the link between the smart nail and the data associated therewith. Users can terminate the link manually online, for example by logging into a web portal using their account, and instructing the system to terminate the link. Alternatively, if the nail falls off the finger, the RFID tag can be automatically terminated using a sensor which senses a disconnection between the artificial nail and the finger, and automatically disables the RFID tag.

Figure 8:
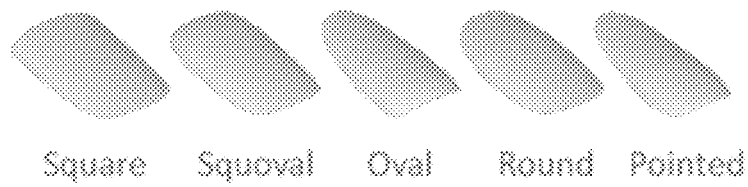
FIG. 8 illustrates various different shapes of artificial nails which can be printed.
Figure 9:
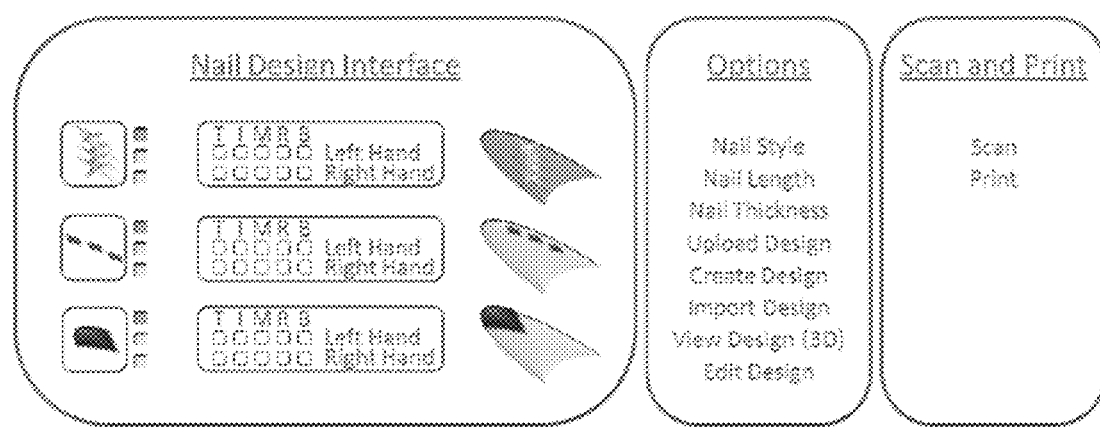
FIG. 9 is a schematic illustrating a user interface allowing users to design their custom-fit artificial nails, according to an embodiment.
Figure 10:
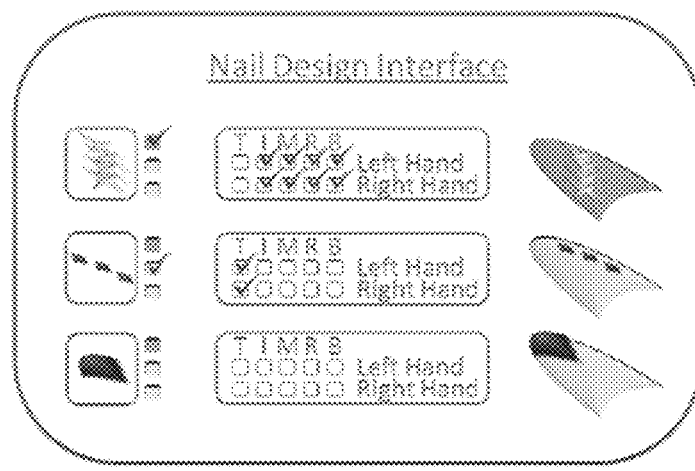
FIG. 10 is a schematic illustrating the user interface of FIG. 9 with several design options selected.

With reference now to FIGS. 8, 9 and 10, the UI module can allow users to operate the 3DSIP system and perform functions such as nail design and initiating/controlling the scanning and printing processes. The nail design interface allows the user to select, import, and create nail styles. The digital interface allows the user to create a design, import a design (e.g. internet, usb, etc. . . . ), or use a design that exists on the system; thereby allowing all types of designs to be implemented and created through the nail design interface. The designs can be viewed and edited on the digital UI prior to finalizing the design. As described elsewhere herein, the UI can be presented on a user device, such as a computer, laptop or mobile device. Designs can be applied to all or specific nails (i.e. the thumb (T), index (I), middle (M), ring (R), and baby (B) on the right and left hand can have the same or different designs based on the user's selection). The length, thickness, and style (e.g. pointed tip and flat tip) of the nails can be customized. FIG. 8 shows typical nail styles that are available. Note that the user is not limited to the nail styles available on the system and can create any nail style for print and application. Note that the nail length can increase beyond the length of the original nail thereby allowing for different nail lengths.

FIGS. 9 and 10 show an example of the nail selection process. As illustrated in FIG. 9, the UI can present the user with a number of nail style options, including selecting a pattern and color, and selecting which individual nail the pattern and color should be applied to. In FIG. 10, a pattern and color of emeralds on pink is selected for the thumb (T) of the right and left hand and silver stars on mauve is selected for the index (I), middle (M), ring (R), and baby (B) of the right and left hand.

As shown in FIG. 9, the UI provides the user with a number of other customization options, such as setting the nail length and thickness. Although not illustrated, it is appreciated that the user could also be presented with other options as well, for example selecting a material, choosing a lamination, and/or selecting an object to embed. The UI further allows users to upload their design (for example for sharing or subsequent use), create a new design, import designs (for example from another user, or from one of their own previous designs), preview the design in 3D, and edit their design. Once the user is content with their design, they can initiate the printing process. The UI also provides the user with the ability to begin the process by initiating the scanning of the user's nails.

It should be understood that data acquired by the 3D scanning module can be used for reasons other than solely for manufacturing custom-fit artificial nails. More particularly, the 3DSIP system can use acquired data to provide medical analyses, detections, and diagnostics based on nail metrics like color, thickness, splitting, concavity, pitting, ridges, dryness, and clubbing. Medical analyses, detections, and diagnostics can also be based on anatomical characteristic and/or anatomical changes of the hand/feet (e.g. swelling, color, texture, dryness, energy, etc.). The system can maintain historical data, and provide medical forecasting, risk assessments, and recommendations. It is appreciated that this functionality can be provided in a standalone system, or be integrated as part of a 3DSIP system to provide augmented functionality thereto.

A number of conditions can be detected and tracked by identifying various features or combination of features of nails scanned by the 3DSIP system. Parts of the nails can be analyzed, or the nail can be analyzed as a whole in order to identify, qualify and/or quantify nail features known to be associated with certain conditions. It is appreciated that such identification can be accomplished using data from a single scan, or using data from multiple scans for increased accuracy, or in order to track progression of a potential condition over time. The detection method can be performed by the 3DSIP through automated medical and image processing algorithms. Individual nail and feature (e.g. anatomical changes, color, thickness, splitting, concavity, pitting, ridges, dryness, and clubbing) models as well as population models based on demographics can be created using image processing software, machine learning, deep learning, and artificial intelligence (AI) and used to differentiate normal from abnormal nails and define the associated conditions (should they exist). If approved by the individual, the data can be linked to their online medical records. An automated quality control system can be used to ensure the integrity of the data.

There are a wide variety of conditions which can be diagnosed by identifying certain nail features. For example, looking at color, green nails could be a sign of bacterial infection; red streaks in the nail bed could be a warning of a heart valve infection; bluish nails could signal low oxygen levels in the blood; dull nails could indicate a vitamin deficiency; white nails may signal liver disease, such as hepatitis; and dark stripes on top (Terry's nails) could signal aging or congestive heart failure. Looking at thickness, thickened nails that are otherwise normal can signal lung disease; thick and rough-textured nails can signal a fungal infection; thick and separated nails may mean thyroid disease or psoriasis; and unusual thickness may also be a symptom of a circulation problem. Identifying split nails can aid in diagnosing folic acid, Vitamin C, and protein deficiencies and/or chronic malnutrition. Moreover, split nails combined with a pitted nail bed can signal psoriasis. Identifying nail concavity (spoon) can indicate psoriasis; connective tissue disorder; alopecia areata (an autoimmune disorder that causes hair loss); or zinc deficiency (pit seems to form a line across the middle of the nail). Identifying ridges can be indicative of iron deficiency; inflammatory arthritis; or Lupus (for red lines at the base of the nails). Identifying dry/brittle nails can indicate thyroid disease (dry nails that crack and split easily) or fungus (dry or crumbly nails). Finally identifying Clubbing (a painless increase in tissue around the ends of the fingers, or inversion of the nail) can indicate lung disease, especially with existing trouble breathing; inflammatory bowel disease; liver disease.

Furthermore, a number of conditions can also be diagnosed by evaluating overall nail appearance. For example, white nails could indicate liver diseases, such as hepatitis; yellowish, thickened, slow-growing nails could indicate lung diseases, such as emphysema; yellowish nails with a slight blush at the base could indicate diabetes; half-white, half-pink nails could indicate kidney disease; red nail beds could indicate heart disease; pale or white nail beds could indicate anaemia; pitting or rippling of the nail surface could indicate psoriasis or inflammatory arthritis; clubbing could indicate lung diseases; irregular red lines at the base of the nail fold could indicate lupus or connective tissue disease; and dark lines beneath the nail could indicate melanoma.

In some implementations, blockchain is applied to ensure security, privacy, and interoperability of our data and system.

The diagnosis of other conditions not mentioned above may also be accomplished with the help of identifying the features mentioned above, in addition to other identifiable nail features not specifically mentioned. The 3DSIP can also be updated as new diagnostic information becomes available, to better diagnose conditions using more detailed analysis of features, or by identifying different features. It is appreciated that the analysis of features need not be limited to the nails, and can further include other parts of hands or feet captured during the nail scanning process.

As mentioned above, the 3DSIP system has a variety of connections allowing it to communicate with other devices and networks, such as with a cloud service. Such connections can allow for enhancing the user experience, for example by allowing the user to: save and readily access their customized nail designs through the internet; print customized nail designs at any location (e.g. an individual can login to their online dashboard and choose a prior or new design to print for their appointment); trade nail designs (e.g. trade with celebrities, friends, nail artists, online designs); have a personal online dashboard that stores individual nail measurements and a history of nail designs; be a part of online market to purchase nail designs; link to social media platforms like Facebook, Instagram, and Twitter for promotions; assess their medical health; obtain pertinent medical forecasting, risk assessments, and recommendations; and link their medical data that was obtained through the 3DSIP system to an online medical system. The 3DSIP system can further allow individuals to promote their customized nails online through Facebook, Instagram, Twitter, and other social media platforms.

Although certain embodiments and exemplary hardware configurations were described herein, it is appreciated that a number of other configurations can be provided without departing from the scope of the invention. While specific embodiments have been described and illustrated, it is understood that many changes, modifications, variations and combinations thereof could be made without departing from the scope of the invention.

What is claimed is:

1. A system for manufacturing a custom fit artificial surface for a user's anatomical extremity, the system comprising:
   a 3D surface scanning module;
   a 3D manufacturing module; and
   a central processing module operatively connected to the 3D surface scanning module and the 3D manufacturing module, the central processing module being operable to:
   operate the 3D surface scanning module to obtain an image of the user's anatomical extremity;
   process the image to create an input 3D model of the anatomical extremity of the user;
   generate an output 3D model corresponding to an artificial surface matching dimensions of the user's anatomical extremity according to the 3D input model;
   operate the 3D manufacturing module to manufacture the artificial surface according to the output 3D model;
   process the image to identify one or more predetermined features of the user's anatomical extremity;
   generate medical data by correlating the identified predetermined features of the user's anatomical extremity with known medical conditions, in order to diagnose a medical condition of the user which is known to exhibit the identified features as a symptom; and
   wherein the 3D manufacturing module comprises an embedder configured to embed a premanufactured object into the artificial surface during the 3D manufacturing process; and wherein the premanufactured object comprises an embedded device or a sensor or both, and wherein the central processing system is further operable to link to the embedded device or the sensor with a user account stored on a server.

2. The system according to claim 1, wherein the embedded device or the sensor comprises an RFID chip.

3. The system according to claim 2, wherein the sensor is configured to detect the artificial surface becoming detached and to disable the RFID chip upon detecting the artificial surface becoming detached from the anatomical extremity.

4. The system according to claim 1, further comprising a network module operatively connected to the central processing module, the central processing module being configured to communicate with an online medical system over the network module in order to link the generated medical data therewith; and wherein the central processing module is configured to transmit the medical data to an external server over the network module in order to allow a person to access the medical data remotely and assess medical health information of the user.

5. The system according to claim 1, wherein the central processing module is further configured to generate at least one of a medical forecast, a medical risk assessment and a recommendation based on the generated medical data.

6. The system according to claim 1, wherein the central processing module is configured to store a history of scans by the user, and combine said history of scans in order to generate a model of the user's anatomical extremity; and wherein the central processing module is configured to analyse the history of scans in order to track a progression of the medical condition of the user.

7. The system according to claim 1, wherein the central processing module is configured to store a history of scans by a plurality of users, and combine said history of scans in order to build a population model representing variability across the plurality of users; and wherein the central processing module is configured to compare the image of the user's anatomical extremity with the population model in order to determine differences therebetween.

8. The system according to claim 1, wherein processing the image to identify predetermined features of the user's anatomical extremity comprises identifying anatomical extremity features selected from the group consisting of: anatomical changes, color, thickness, splitting, concavity, pitting, ridges, dryness and clubbing.

9. The system according to claim 1, wherein the 3D surface scanning module comprises at least one sensor of a first type operable to capture shapes of the anatomical extremity of the users and at least one sensor of a second type operable to capture surface features of the anatomical extremity of the user.

10. The system according to claim 1, wherein the 3D manufacturing module is operable to add at least one medicinal ingredient to the manufactured artificial surface; and wherein the central processing module is operable to select the medicinal ingredient based on the medical condition diagnosed for the user.

11. The system of claim 1, wherein the user is a human.

12. The system of claim 1, wherein the anatomical extremity is a nail and the artificial surface is an artificial nail.

13. The system of claim 1, wherein the anatomical extremity is part of a foot of the user.

14. The system of claim 1, wherein the system is configured to manufacture a plurality of the artificial surfaces for respective anatomical extremities of the user.

15. The system of claim 1, wherein the 3D manufacturing module is configured to use one or more techniques selected from the group consisting of additive manufacturing, extrusion, light polymerized manufacturing, powder bed manufacturing, laminated manufacturing, wire fed manufacturing, Stereolithography (SLA), Digital Light Processing (DLP), Fused Deposition Modeling (FDM), Selective Laser Sintering (SLS), Selective Laser Melting (SLM), Electronic Beam Melting (EBM) and Laminated Object Manufacturing (LOM).

16. The system of claim 1, wherein the 3D manufacturing module is a 3D printing module.

17. A system comprising:
a 3D surface scanning module;
a 3D manufacturing module; and
a central processing module operatively connected to the 3D surface scanning module and the 3D manufacturing module, the central processing module being operable to:
  operate the 3D surface scanning module to obtain an image of the user's anatomical extremity;
  process the image to create an input 3D model of the anatomical extremity of the user;
  generate an output 3D model corresponding to an artificial surface matching dimensions of the user's anatomical extremity according to the 3D input model;
  operate the 3D manufacturing module to manufacture the artificial surface according to the output 3D model;
  process the image to identify one or more predetermined features of the user's surface;
  generate medical data by correlating the identified predetermined features of the user's anatomical extremity with known medical conditions, in order to diagnose a medical condition of the user which is known to exhibit the identified features as a symptom; and
wherein the 3D manufacturing module comprises an embedder configured to embed a premanufactured object into the artificial surface during the 3D manufacturing process, the premanufactured object being an embedded device or a sensor or a combination thereof.

18. The system according to claim 17, wherein the premanufactured object is configured to detect the artificial surface becoming detached from the anatomical extremity.

19. The system according to claim 17, wherein the premanufactured object is embedded within a thickness of the artificial surface.

20. The system according to claim 17, wherein the premanufactured object is positioned in an outer surface of the artificial surface and is thus visible.

* * * * *